(12) United States Patent
Chang et al.

(10) Patent No.: US 6,960,178 B2
(45) Date of Patent: *Nov. 1, 2005

(54) APPARATUS FOR ENHANCED PLASMAPHERESIS AND METHODS THEREOF

(75) Inventors: Yu-An Chang, Irvine, CA (US); Daniel Duff, Irvine, CA (US); Hosheng Tu, Newport Beach, CA (US)

(73) Assignee: XEPMED, Inc., Los Angeles, CA (US)

( * ) Notice: Subject to any disclaimer, the term of this patent is extended or adjusted under 35 U.S.C. 154(b) by 535 days.

This patent is subject to a terminal disclaimer.

(21) Appl. No.: 10/195,814

(22) Filed: Jul. 15, 2002

(65) Prior Publication Data

US 2002/0183677 A1 Dec. 5, 2002

Related U.S. Application Data

(63) Continuation-in-part of application No. 09/496,613, filed on Feb. 2, 2000, now Pat. No. 6,423,023.

(51) Int. Cl.[7] .................. A61M 37/00; B01D 33/00; B01D 24/28
(52) U.S. Cl. .............. 604/6.04; 604/6.09; 210/359; 210/385; 210/780
(58) Field of Search .............. 604/6.04, 6.09, 604/5.04, 6.03; 210/637, 561, 247, 209, 297, 385, 359, 490, 107, 109, 321.87, 645, 767, 483, 494, 360.1, 787, 780–782

(56) References Cited

U.S. PATENT DOCUMENTS

| | | |
|---|---|---|
| 3,705,100 A | 12/1972 | Blatt et al. |
| 4,191,182 A | 3/1980 | Popovich et al. |
| 4,212,742 A | 7/1980 | Solomon et al. |

(Continued)

OTHER PUBLICATIONS

B R Jaeger et al. "H.E.L.P. Apheresis for the Treatment of Acute Myocardial Infarction" 73rd European Atherosclerosis Society Congress Proceedings, # 150, Salzburg, Austria Jul. 7–10, 2002.

C Otto et al., "Long–Term Reduction of C–Reactive Protein by LDL Apheresis" 73rd European Atherosclerisis Society Congress Proceedings, # 185, Salzburg, Austria Jul. 7–10, 2002.

G A Konovalov et al. "LDL–Apheresis by Immunoadsorption With LDL Lipopak Columns can L0ead Stabilization and Even regression of Atherosclerotic Plaques in Coronary Arteries" 73rd European Atherosclerosis Society Congress Proceedings, # 259, Salzburg, Austria, Jul. 7–10, 2002.

P.M. Moriarty et al. "A Study to Demonstrate the Utility of HELP LDL Apheresis Treatment for Patients With Non–ST Elevation Acute Coronary Syndrome" 73rd European Atherosclerosis Society Congress Proceedings # 511, Salzburg, Austria, Jul. 7–10, 2002.

K.M. Kostner et al. "A Novel Extracorporeal Plasma Delipidation Procedure for the Treatment of Atherosclerosis" 73rd European Atherosclerosis Society Congress Proceedings # 754, Salzburg, Austria, Jul. 7–10, 2002.

*Primary Examiner*—Angela D. Sykes
*Assistant Examiner*—Leslie R. Deak

(57) ABSTRACT

An apparatus and methods for enhanced plasmapheresis comprising a filter membrane under an orbital motion or movement that has optimal local shear forces and maximum plasma flow output. The methods for biological separation and therapies comprise platelet collection, viral particle removal, cell washing and processing for stem cell selection, bone marrow purging, red blood cell collection, auto-transfusion, auto-immune disease treatment, selective macro-molecule removal, toxin removal, LDL removal, extracorporeal plasma delipidation, and the like.

19 Claims, 4 Drawing Sheets

U.S. PATENT DOCUMENTS

| | | |
|---|---|---|
| 4,735,726 A | 4/1988 | Duggins |
| 5,034,135 A | 7/1991 | Fischel |
| 5,194,145 A | 3/1993 | Schoendorfer |
| 5,234,608 A | 8/1993 | Duff |
| 5,376,263 A | 12/1994 | Fischel |
| 5,529,691 A | 6/1996 | Brown |
| 5,695,653 A * | 12/1997 | Gsell et al. ............... 210/767 |
| 5,744,047 A * | 4/1998 | Gsell et al. ............... 210/767 |
| 6,238,795 B1 * | 5/2001 | Strom et al. ............. 428/403 |
| 6,423,023 B1 * | 7/2002 | Chang et al. ............ 604/6.04 |

* cited by examiner

APPARATUS FOR ENHANCED PLASMAPHERESIS AND METHODS THEREOF

RELATIONSHIP TO COPENDING APPLICATIONS

This patent application is a continuation-in-part of application Ser. No. 09/496,613 filed Feb. 2, 2000 now U.S. Pat. No. 6,423,023, entitled "Method and Apparatus for Enhanced Plasmapheresis", incorporated herein by reference in its entirety.

TECHNICAL FIELD OF THE INVENTION

The present invention generally relates to medical apparatus and methods for separating a suspension of plasma alone and/or with platelets from whole blood. More particularly, the invention relates to an apparatus and methods for enhanced plasmapheresis comprising a filter membrane under an orbital motion that has optimal local shear forces and maximum plasma flow output.

BACKGROUND OF THE INVENTION

Separation of blood into a plasma fraction and a cellular component fraction is desirable for many medical reasons. For example, separation of blood into plasma fractions and cellular component fractions provides for a collection of plasma alone, with the cellular component being returned to the donor with an optional suitable portion of replacement fluid. Thus continuous plasmapheresis provides for the collection of plasma from donors without the removal of the cellular components of the blood. Plasma donation from a patient or donor is generally allowed about twice a week whereas the whole blood donation is allowed once in every two months. Secondly, continuous plasmapheresis can be used therapeutically to remove pathologic substances contained in the plasma portion of the blood, as disclosed by Popovich et al. in U.S. Pat. No. 4,191,182. This can be accomplished by separating the cellular components from the diseased plasma and returning the cellular components to the patient in admixture with a suitable replacement fluid, or by further fractionating the patient's plasma to remove the unwanted substances and returning a major portion of the patient's plasma with the cellular components.

The separation of blood into cellular component fractions and plasma fractions has inherently some difficulties and complications. A brief discussion of the makeup of blood is shown herein for illustration purposes. Approximately 45% of the volume of blood is in the form of cellular components. These cellular components include red cells, white cells and platelets. If cellular components are not handled correctly, the cells may lose their functionality and become useless. Plasma makes up the remaining 55% of the volume of blood. Basically, plasma is the fluid portion of the blood which suspends the cells and comprises a solution of approximately 90% water, 7% protein and 3% of various other organic and inorganic solutes. As used herein, the term "plasmapheresis" refers to the separation of a portion of the plasma fraction of the blood from the cellular components thereof.

Ultrafiltration has been widely used on a batch-type or continuous basis as a substitute for, or in combination with, dialysis methods in artificial kidneys and the like. In any plasmapheresis-type process effected by ultrafiltration there are various problems which occur during the fractionating of the blood by passing it in a parallel flow pattern over a membrane surface, with a transmembrane pressure sufficient to push the plasma portion of the blood therethrough, while allowing the cellular component portion of the blood to remain thereon. One of these problems is that the flow rates must be controlled fairly closely. Thus, if the flow rate employed is too fast at any moment or at any specific region, detrimental turbulence may occur and excess shear force may cause unwanted hemolysis resulting in general destruction of cellular components. On the other hand, if the flow rate and the transmembrane pressure are not controlled adequately the cellular and macromolecular components of the blood will tend to clog up the membrane thus significantly slowing the ultrafiltration rate. Such clogging can also cause hemolysis to occur.

Along the blood flow route in a plasmapheresis apparatus, plasma continues to pass through the filter membrane while cellular component remains in the blood stream. At the downstream region of the separation process, the blood becomes more viscous and the separation efficiency decreases drastically. This fouling effect or "concentration polarization" phenomenon becomes obvious in a conventional batch-wise or continuous ultrafiltration process. For example, U.S. Pat. No. 3,705,100 to Blatt et al., issued Dec. 5, 1972, discloses a process and apparatus for a blood fractionating process on a batch basis. Furthermore, U.S. Pat. No. 4,191,182 to Popovich et al., issued Mar. 4, 1980, discloses a means for continuous plasmapheresis including a blood input pumping means and a plasma outflow pumping means. Though the average flow rate of the disclosed device is within the non-hemolysis range, the local flow rate and its shear force at any moment and/or at any specific region of the filter membrane may not be adequate to effect the most efficient plasmapheresis. Concentration polarization usually occurs at a later stage in a batch plasmapheresis or at a downstream region in a continuous plasmapheresis.

To compensate for the concentration polarization drawbacks, Solomon et al. in U.S. Pat. No. 4,212,742 discloses a filtration device employing a microporous filtration membrane. The filtration flow channels along the surface of the upstream side of the membrane wall are provided with gradually and uniformly increases from the inlet end to the outlet end of the flow channel, whereby the membrane wall shear force of the suspension in laminar flow through the flow channel gradually and uniformly varies along the length of the flow channel from a maximum value at its inlet end to a minimum value at its outlet end. However, Solomon et al. device requires enormous membrane surfaces for blood plasma separation which appear not economically practical.

For the purposes of increasing the transmembrane pressure drop hopefully to catch a higher separation efficiency and a less concentration polarization effect, Fischel in U.S. Pat. No. 5,034,135, Schoendorfer in U.S. Pat. No. 5,194,145, Duff in U.S. Pat. No. 5,234,608, Fischel in U.S. Pat. No. 5,376,263, and Brown in U.S. Pat. No. 5,529,691 all disclose a blood separating system comprising high rotational velocity flow applying centrifugal forces aiming for added transmembrane pressure drop. During high centrifugal rotation, a portion of the cellular components may undesirably remain in the rotational device or inside pores of the filter membrane for a prolonged time and may subject to hemolysis, cellular damage or membrane clogging. For centrifugal-type separation processes, the local shear force for the cellular components of the blood concentrate fraction is the highest at about the periphery of the separation apparatus, such as a spinner-type device and the like. The requirement of a proper shear force at the outer-most region in a rotational separator apparently limits the size, and therefore the capacity, of the separation apparatus or the spinner.

Alternately, to create adequate local flow rate and subsequently local shear force in a plasmapheresis process, Duggins in U.S. Pat. No. 4,735,726 discloses a process for continuous plasmapheresis comprising conducting blood over a microporous membrane in a reciprocatory pulsatile flow pattern. The pulsatile flow is known to cause certain degrees of turbulence as the pulsatile flow rate changes constantly which may possibly cause cell damage and membrane clogging. Duggins discloses a damage-controlling method to compensate for the shortcomings of the pulsatile flow in a continuous plasmapheresis by reducing the transmembrane pressure difference to below zero during each forward and reverse flow. This additional equipment setup and control mechanism for repetitively reversing the transmembrane pressure difference makes this process less economically attractable.

There is an urgent clinical need to provide an efficient plasmapheresis process by minimizing the cellular damage while increasing the flow output. This may be achievable by controlling the local flow rate and local shear force of a filtration apparatus comprising a filter membrane with an orbital motion to minimize problems of undesired turbulence and concentration polarization in a conventional separating apparatus.

SUMMARY OF THE INVENTION

In general, it is an object of the present invention to provide a method and an improved apparatus for enhanced plasmapheresis. It is another object of the present invention to provide an improved separating apparatus for blood fractionation, for cell washing of blood autotransfusion, for bone marrow transfusion, for peripheral stem cell transfusion, and the like. It is a further object of the present invention to provide a filtration system and methods thereof comprising a fluid supply containing filtrate and particulate constituent. The "particulate constituent" in a broad sense is herein meant to indicate the remaining substance other than the filtrate from the fluid supply.

Enhanced continuous plasmapheresis is accomplished by continually feeding a blood supply through a filtration chamber to effect separation of plasma components and cellular components. The blood passes in essentially parallel to the plane of the filtration membrane at flow rates sufficient to create shear stress across the membrane in the order of 10 to 2,000 dynes/cm$^2$, a preferred range being from about 100 to about 1,000 dynes/cm$^2$. The membrane has a pore size, pore shape, and cells affinity sufficient to allow the plasma components to pass therethrough but retain cellular components thereon. Generally pore sizes of from 0.2 to 1.0 microns are preferred for plasma or platelet separation. Transmembrane pressure of from about 10 mmHg to about 1,000 mmHg are employed to separate the blood into cellular components and plasma fractions. With assistance of the orbital motion of the membrane, the local flow rate and shear stress can be controlled, resulting in a narrower range of the transmembrane pressure that has lower hemolysis and lower plugging propensity.

In order to accomplish the enhanced plasmapheresis, a filtration system may comprise a filtration chamber having a hollow interior enclosed by a first plate, a second plate, and a flexible seal element between the first plate and the second plate, wherein the first plate is either essentially parallel to or at an acute angle to the second plate so as to form a chamber gap for the hollow interior. The filtration system further comprises a fluid supply means for supplying a fluid containing filtrate and particulate constituent; a means for directing the fluid supply into the hollow interior; and a filtrate collecting means for directing the filtrate passing through the filter membrane means to a collecting means and a particulate constituent collecting means for directing from the chamber gap a remaining constituent of the fluid supply out of the chamber. The second plate comprises filter membrane means for separating filtrate from the particulate constituent, and wherein the second plate is detachably coupled to a non-rotational drive structure that controls the second plate in an orbital motion in reference to a center axis of the first plate.

The term of "orbital motion" as used in the patent application refers to a motion that moves back and force between two points in a continuous manner, wherein the route of the forward movement may either partially overlap or not overlap the route of the backward movement. However, the "orbital motion" is different from "rotation" in this patent application. "Rotation" is defined as a movement in such a way that all particles follow circles with a common angular velocity about a common axis. (Webster's New Collegiate Dictionary, G & C Merriam Co. 1980)

In a preferred embodiment, a blood filtration apparatus may comprise a chamber having a hollow interior enclosed by a first plate, a second plate, and a flexible seal element between the first plate and the second plate, wherein the first plate is either essentially parallel to or at an acute angle to the second plate so as to form a chamber gap for the hollow interior; wherein the second plate comprising filter membrane means for separating plasma constituent from the blood, wherein the second plate is detachably coupled to a non-rotational drive structure that controls the second plate in an orbital motion in reference to a center axis of the first plate. The blood filtration apparatus further comprises means for directing a blood supply into the chamber gap; means for directing the plasma constituent passing through the filter membrane means to a collecting means; and means for directing from the chamber gap a remaining constituent of the blood out of the chamber.

In a still further embodiment, a blood filtration method for use in separating filtrate from blood supply comprises the steps of (a) feeding the blood supply into a chamber having a hollow interior enclosed by a first plate, a second plate, and a flexible seal element between the first plate and the second plate, wherein the first plate is either essentially parallel to the second plate or at an acute angle to the second plate so as to form a chamber gap for the hollow interior; the second plate comprising filter membrane means for separating filtrate constituent from the blood, wherein the second plate is detachably coupled to a non-rotational drive structure that controls the second plate in an orbital motion in reference to a center axis of the first plate; (b) initiating orbital motion of the second plate by the non-rotational drive structure to effect enhanced separation of filtrate from blood supply; (c) collecting the filtrate constituent passing through the filter membrane means; and (d) discharging a remaining constituent of the blood from the chamber gap out of the chamber. The blood supply may comprise at least one component selected from the group consisting of red blood cell, white blood cell, and platelet.

It is therefore some aspect of the present invention to provide an apparatus and enhanced apheresis methods thereof for biological separation and therapies, such as platelet collection, viral particle removal, cell washing and processing for stem cell selection, bone marrow purging, red blood cell collection, auto-transfusion, auto-immune disease treatment, selective macro-molecule removal, toxin removal, LDL removal, extracorporeal plasma delipidation, and the like.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 4, what is shown is an embodiment of the enhanced separation process employing a separation chamber comprising a filter membrane under an orbital motion. The enhanced separation process is particularly applicable for plasmapheresis and other medical applications, such as for blood fractionation, for blood autotransfusion, for bone marrow transfusion, for peripheral stem cell transfusion, and the like.

Figure 1:
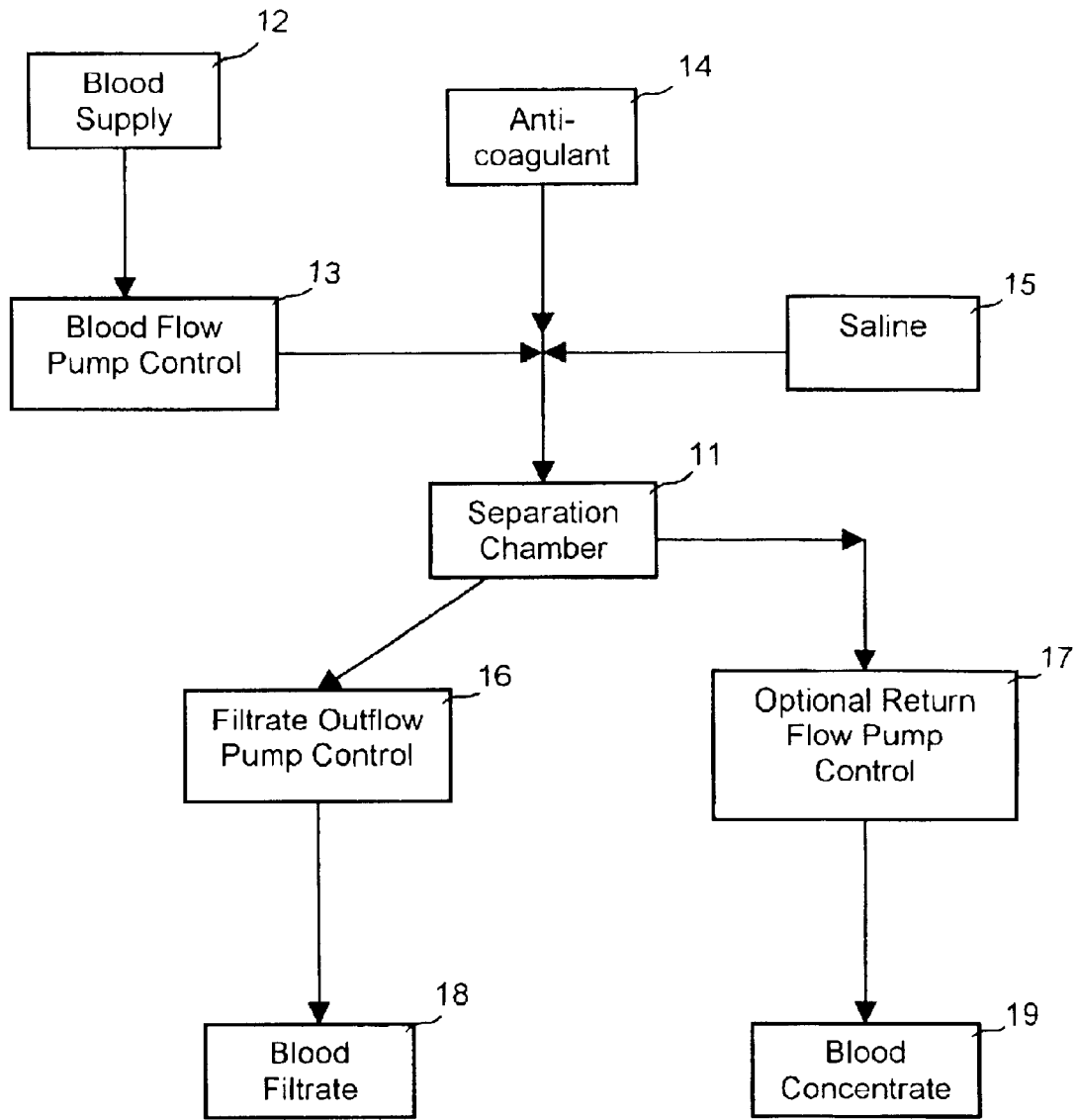
FIG. 1 is a schematic diagram of an enhanced blood separation process employing a separation chamber comprising a filter membrane under an orbital motion of the present invention.

FIG. 1 shows a schematic diagram of an enhanced blood separation process employing a separation chamber comprising a filter membrane under an orbital motion of the present invention. The blood supply 12 to the apparatus 11 may comprise fresh whole blood, thawed blood, or partially fractionated blood. The blood supply is fed to the separation chamber 11 via a blood flow pump control 13 or other means for directing a blood into the separation chamber 11. To maintain the blood supply from coagulation, anticoagulant 14 may optionally be added into the blood supply at an appropriate point of the blood supply feeding line. Similarly, saline 15 may optionally be added during the blood-feeding step. A positive pressure is generally maintained during the plasmapheresis of the present invention. The pressure difference across the membrane is preferably in the range of 10 to 1000 mm of mercury. The pressure difference is controlled by the flow rates of the blood flow pump control 13, the filtrate outflow pump control 16 and/or the return flow pump control 17.

Blood filtrate 18 is collected from the opposite side of the filter membrane, wherein the filtrate collecting means is completely isolated from communication with the blood supply. The filtrate is collected from the separation chamber 11 via a filtrate outflow pump control 16 or other means for directing the plasma constituent passing through the filter membrane. Blood concentrate 19 or the cellular constituent portion is withdrawn from the separation chamber 11 via an optional return flow pump control 17 or other means for directing a remaining constituent of the blood out of the chamber.

The pressure drops across the filter membrane can be adjusted by manually adjusting one or more of the flow pump controls 13, 16, and 17, or by providing automatic adjusting mechanisms. The pressure drop may be measured by an optional differential pressure indicator and/or controlled by the automated adjusting mechanisms.

Figure 2:
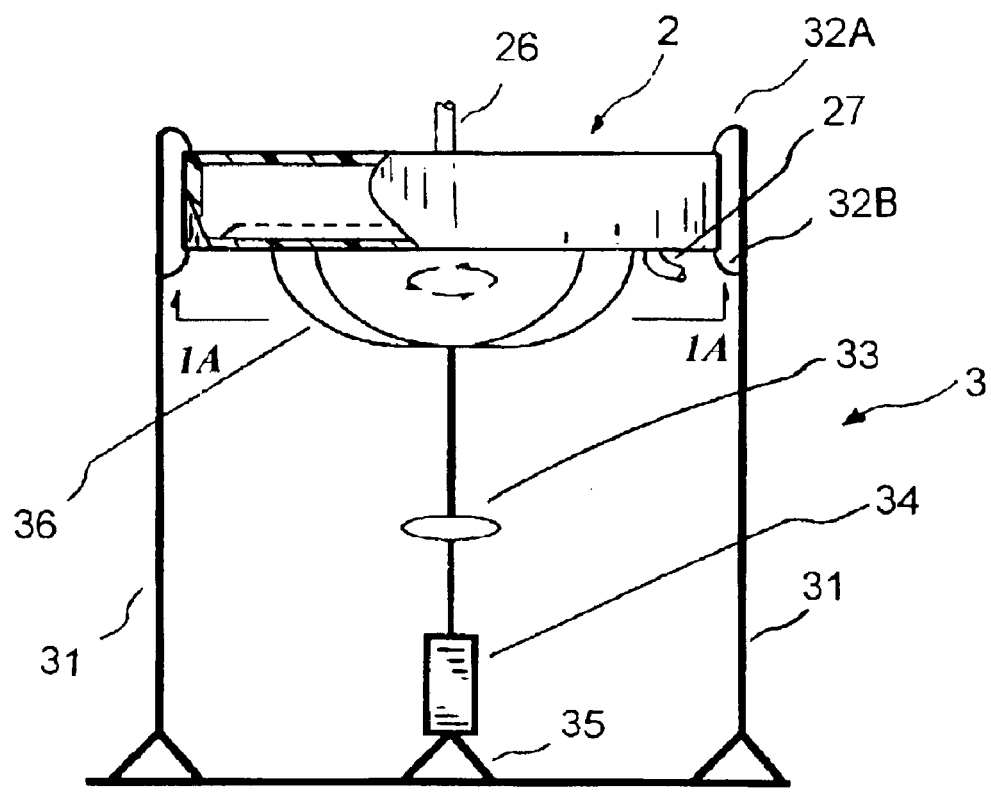
FIG. 2 is an illustrative setup of an enhanced blood separation process employing a separation chamber comprising a filter membrane under an orbital motion.

FIG. 2 shows an illustrative setup of an enhanced blood separation process employing a separation chamber comprising a filter membrane under an orbital motion. A plasmapheresis setup comprises a supporting installation 3 that can be rolled away or placed at any convenient location and a removable blood filtration apparatus 2. The supporting installation 3 comprises a plurality of supporting poles 31 and a rotatable means 34 for generating orbital motion through a non-rotational structure 33 to the blood filtration apparatus 2. The rotatable means 34 may be selected from the group consisting of a rotatable magnetic motor, a rotatable mechanical motor and the like, wherein the rotatable means 34 is firmly attached to the supporting installation 3 via an attachment 35.

Each supporting pole 31 has a couple of grabbing pins 32A, 32B for securely and firmly holding the blood filtration apparatus 2 in place when the removable blood filtration apparatus 2 is placed into the supporting installation 3. The grabbing pins 32A, 32B are generally equipped with a spring-like mechanism for releasing the blood filtration apparatus 2 when the apparatus needs to be removed from the supporting installation 3. The supporting poles 31 are so designed that the blood filtration apparatus 2 when placed into slots of the grabbing pins 32A, 32B is always at a level without undue vibration caused by the rotatable means 34.

The separation chamber 4 may be installed horizontally, vertically or at any angle. However, for space-saving purposes and taking into consideration of gravity, a preferred setup is a horizontal separation chamber detachably coupled to a vertical non-rotational structure 33.

In an illustrative example, a mechanical motor is used as the rotatable means 34. One end of an elongate shaft is secured to an axis of the mechanical motor while the end of the elongate shaft has a cam. The non-rotational drive structure 33 intimately contacts an edge of the cam and is indirectly coupled to the rotatable means 34 for generating orbital motion to the second plate. Therefore, when the cam rotates, the non-rotational drive structure 33 moves in an orbital motion. The frequency of the orbital motion is related to the rotational frequency of the motor while the off-center distance of the orbital motion is related to the diameter and shape of the cam.

Figure 3:
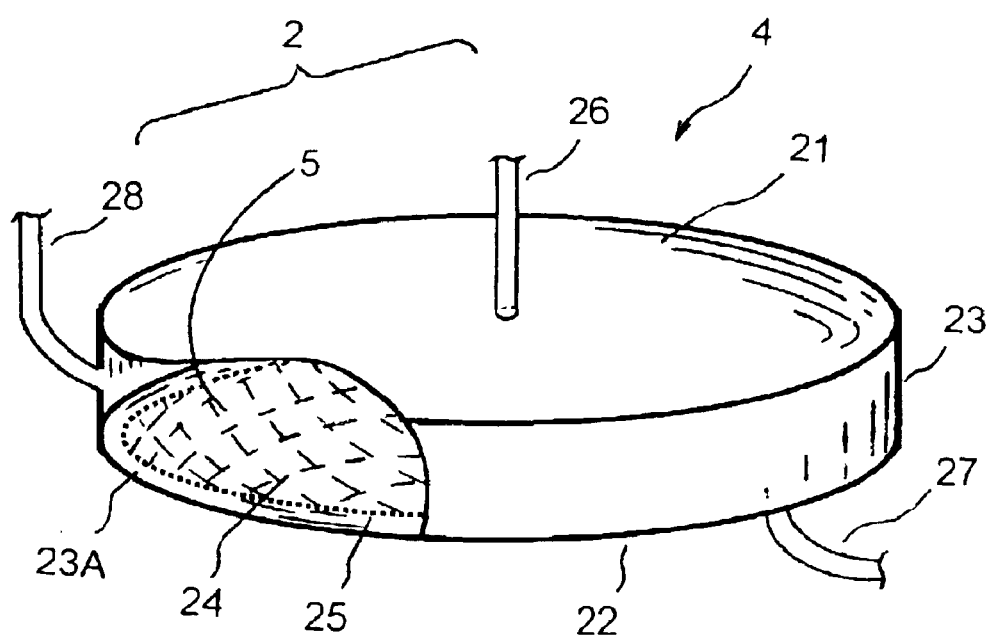
FIG. 3 is a perspective view of the blood filtration apparatus comprising the separation chamber having a filter membrane.

FIG. 3 shows a perspective view of the blood filtration apparatus 2 comprising a separation chamber 4 having a filter membrane 24. The blood filtration apparatus 2 comprises a separation chamber 4, a means 26 for directing a blood into the chamber gap, a means 27 for directing the plasma constituent passing through the filter membrane means to a collecting means, and a means 28 for directing from the chamber gap a remaining constituent of the blood out of the separation chamber 4.

The separation chamber 4 comprises a hollow interior 5 enclosed by a first plate 21, a second plate 22, and a flexible seal element 23 between the first plate 21 and the second plate 22, wherein the first plate 21 is either essentially parallel to or at an acute angle to the second plate 22 so as to form a chamber gap for the hollow interior 5. The second plate 22 comprises filter membrane means 24 for separating plasma constituent from the blood, wherein the second plate 22 is detachably coupled to a non-rotational drive structure 33 that controls the second plate 22 in an orbital motion in reference to a center axis of the first plate 21. The chamber 4 is generally detachable from the non-rotational drive structure 33.

The location of the means 26 for directing a blood into the chamber gap may be selected from the group consisting of at about a center of the first plate, at about periphery of the first plate, and at about a corner of the first plate. Similarly, the location of the means 27 for directing the plasma constituent to a collecting means may be selected from the group consisting of at about periphery of the second plate, at about a center of the second plate, and at about a corner of the second plate. The above-mentioned location is determined by the application, the design and the construction of the blood filtration apparatus. In a preferred setup for a horizontal separation chamber 4, the means 26 for directing a blood supply 12 into the chamber gap may be from the top of the separation chamber downward toward the filter membrane 24 or from the bottom of the separation chamber upward toward the filter membrane. To maintain the cellular components in a suspension mode by gravity, the means for blood supply upward toward the separation membrane may be preferred.

In one preferred embodiment, the acute angle between the first plate and the second plate is in the range of 1 degree to 40 degrees so that the concentration polarization effect is minimized. The acute angle may preferably be in the range of 1 degree to 15 degrees. The acute angle may be measured from one side of the two plates to another side of the plates, from the center to the periphery of the plates or in other arbitrary manner.

The flexible seal element 23, 23A may be selected from the group consisting of silicone, polyurethane, latex, Nylon, polyvinyl chloride, polyimide, polycarbonate, polyacrylate, polymethacrylate, polystyrene, polyethylene, polypropylene, their mixture, and their copolymer. The flexible seal element of the present invention refers to a seal material that is flexible and fluid-tight so that the second plate 22 can move in an orbital motion in reference to a center axis of the first plate 21.

The filter membrane means 24 for separating the plasma constituent from the blood may be selected from the group consisting of nylon membrane, polycarbonate membrane, polysulfone membrane, polyimide membrane, oval pore membrane, micro-fabricated membrane, tract-edged membrane, a combination of the above and the like. In a preferred embodiment, the filter membrane means 24 is partially attached to the second plate 22 at periphery 25 of the second plate 22 so that a space below the filter membrane 24 has no fluid communication with the chamber interior 5 except through the membrane 24 itself. The periphery 25 of the second plate 22 is joined with the flexible seal element 23 by a flexible seal material 23A so that the two plates 21, 22 can move orbitally, but not rotate, relative to each other.

In order to maximize the separation efficiency, the separation chamber can be in a round shape or in other appropriate shape to take advantages of the orbital motion or movement of the second plate. The filter membrane can also be in a round shape or in other appropriate shape. The filter membrane and its properties for separating blood supply or other solute-containing fluid are well known to one of ordinary skill in the art.

The main purpose of a filter membrane 24 of the present invention is to separate one component in a fluid from other constituents. It is one aspect of the present invention to coat or securely load a substrate onto a filter membrane to enhance separation or apheresis. One example is to coat heparin onto a membrane enabling reducing any clot or platelet adhesion onto the membrane. In another aspect of the present invention, the substrate is an antibody enabling selectively coupling with the corresponding antigen in the solution for effective antigen removal.

The interior surface of the second plate 22 facing the downstream side of the filter membrane 24 may be ribbed and/or studded. It is adapted for allowing the plasma constituent to pass through the filter membrane means onto the spaces between the ribs and/or studs of the interior surface and subsequently to the collecting means 27. The pattern of ribs may be selected from the group consisting of concentric circular ribs, hexagonal ribs, square ribs and the like. The studs can be in any fashion on the interior surface of the second plate. In an alternate embodiment, the middle portion of the filter membrane 24 is detached from the interior surface of the second plate 22. A vibration means for causing the middle portion of the membrane to vibrate so as to minimize membrane clogging during blood filtration may be optionally provided. The vibration means may comprise an electromagnetic mechanism.

To effect the optimal plasma filtration, the filter membrane usually has pores of a size about 0.1 to 30 $\mu$m, preferably on the order of 0.2 to 1.0 $\mu$m. A more preferred range of pore size is around 0.4 to 0.6 $\mu$m. The selection of pore size may vary with the goal of a particular separation process. As exemplary of membranes having the preferred properties for plasmapheresis with an orbital movement are HT 450 polysulfone membrane commercially available from Gelman Sciences, Inc., the polyester and polycarbonate membranes commercially available from Nuclepore Corporation.

The chamber gap may be between 0.001 and 0.1 inch for generating optimal local flow rate and local shear force for plasma filtration process. A preferred range of chamber gap is about 0.03 to 0.06 inch. The optimal shear force for enhanced filtration process of the present invention is a function of a combination of the chamber gap, the flow rates of the fluid supply and the outflow filtrate, and the orbital motion characteristics, wherein the orbital motion characteristics may comprise the orbiting frequency, orbiting distance, and orbiting manners. A preferred range of shear force is around 100 to 1,000 dynes/cm$^2$.

Figure 4:
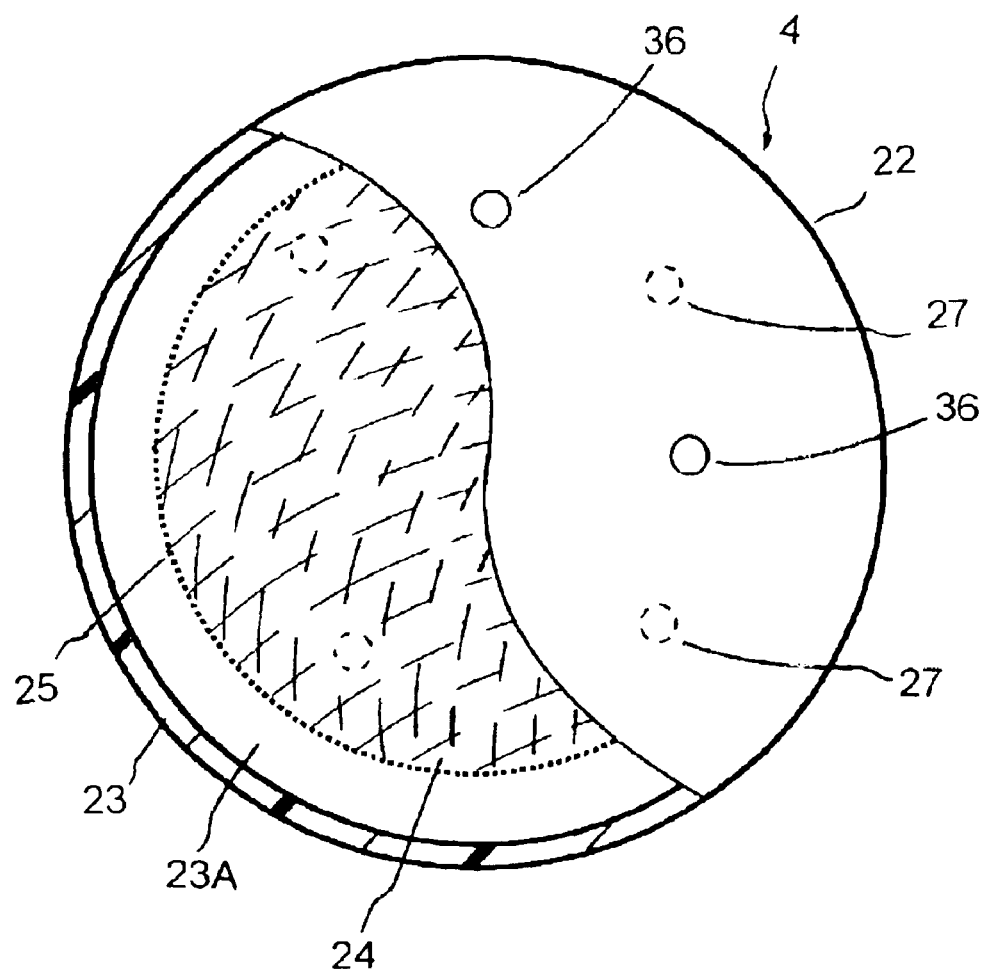
FIG. 4 is a bottom view of the separation chamber for section 1A—1A of FIG. 2

FIG. 4 shows a bottom view of the separation chamber 4 from section 1A—1A of FIG. 2. A plurality of coupling elements 36 is part of the non-rotational drive structure 33, wherein the coupling element 36 is detachably coupled to an exterior side of the second plate 22 of the separation chamber 4 for causing the second plate 22 to have an orbital motion in reference to a center axis of the first plate 21. The orbital motion or movement may be selected from the group consisting of clockwise movement, counter-clockwise movement and a combination of the above. The off-center orbital motion or movement is generally within a range of 0.001 to 1.0 inch distance. More preferably, the off-center orbital motion is in the range of about 0.05 to 0.5 inch distance. In a further embodiment, the orbital motion may be at a frequency within a range of 100 to 50,000 cycles per minute. The frequency of the orbital motion is preferred in the range of 1,000 to 20,000 cycles per minute. The pattern of the orbital motion or movement may be selected from the group consisting of circular shape movement, oval shape movement, peanut shape movement, pear shape movement, and irregular shape movement.

For application, a blood filtration method for use in separating filtrate from blood supply comprises the steps of (a) feeding blood supply into a separation chamber comprising filter membrane means for separating filtrate constituent from the blood; (b) initiating orbital motion of the filter membrane to effect enhanced separation of filtrate from blood supply; (c) collecting the filtrate constituent passing through the filter membrane; and (d) discharging a remaining constituent of the blood out of the separation chamber and/or returning to the donor.

Therapeutic Plasmapheresis for Neurological Disorders

"Therapeutic plasmapheresis" is herein meant as a method for removing toxic or unwanted elements, for example, toxins, viral particle, LDL (low density lipoprotein), metabolic substances, and plasma constituents implicated in disease, such as complement or antibodies, from the blood of a patient. The therapeutic plasmapheresis (also referred as "therapeutic plasma exchange") is performed by removing blood, separating the plasma from the formed elements, and reinfusing the formed elements together with a plasma replacement back to the patient. It is one object of the present invention to provide a method for removing blood from a patient, separating the plasma from the formed elements, filtering the unwanted elements, such as toxins, viral particle, LDL, metabolic substances, and plasma constituents implicated in disease, such as complement or antibodies, and reinfusing the formed elements together with a plasma replacement back to the patient, wherein the filtering step utilizes a blood filtration apparatus characterized by an orbital motion of the present invention.

In one aspect, the ability to remove antibody and other immunologically active elements from the blood has led to the use of therapeutic plasmapheresis as a therapy for neurological conditions in which autoimmunity is believed to play a role. In some aspect of the present invention, the antibody and other immunologically active elements are removed from the blood by loading an antibody-specific antigen or an agent (or agents) that is specific to the immunologically active elements onto the filtering membrane of the present invention. It is estimated that one-half of the 20,000 to 30,000 TPE (therapeutic plasma exchange) procedures performed annually at present in the United States are done on patients with neurological disorders.

Many diseases, including myasthenia gravis, Lambert-Eaton syndrome, Guillain-Barré syndrome and others, are caused by a so-called autoimmune process. In autoimmune conditions, the body's immune system mistakenly turns against itself, attacking its own tissues. Some of the specialized cells involved in this process can attack tissues directly, while others can produce substances known as antibodies that circulate in the blood and carry out the attack. Antibodies produced against the body's own tissues are known as autoantibodies.

It is one object of the present invention to provide a method of treating autoimmune conditions of a patient comprising filtering the patient's blood through a blood filtration apparatus characterized by an orbital motion of the filter membrane means for separating a plasma constituent from the blood of the present invention and returning the cellular components back to the patient. In a further object of the present invention, the method comprises removing autoantibody from the patient's blood.

Delipidation with Enhanced Apheresis

The present invention discloses an apheresis apparatus having an orbital motion for the separation chamber with a proper membrane. In some aspect, the method may comprise processing plasma and removing the LDL (low density lipoprotein) from plasma without touching or damaging blood cells or activating platelet. LDL apheresis may generally include immunadsorption, dextran sulfate adsorption, heparin-induced extracorporeal LDL precipitation, and direct adsorption of lipoproteins, wherein an apheresis apparatus having a membrane-based separation chamber with an orbital motion of the present invention could be used for effective LDL apheresis.

In one embodiment for immunadsorption apheresis, an LDL-specific or LDL-reactive immune factor is loaded onto the filtering membrane of the separation chamber of the present invention, wherein LDL is effectively adsorbed by the LDL-specific or LDL-reactive immune factor upon passing the filtering membrane. In another embodiment for dextran sulfate adsorption, an LDL-specific or LDL-receptive dextran sulfate is loaded onto the filtering membrane of the separation chamber of the present invention, wherein LDL is effectively adsorbed by the LDL-specific or LDL-receptive dextran sulfate upon passing the filtering membrane.

In still another embodiment for heparin-induced extracorporeal LDL precipitation, an LDL-specific or LDL-receptive heparin is loaded onto the filtering membrane of the separation chamber of the present invention, wherein LDL is effectively adsorbed by the LDL-specific or LDL-receptive heparin upon passing the filtering membrane. The heparin-induced extracorporeal LDL precipitation apheresis may further comprise fibrinogen removal.

Jaeger and associates (Proceedings of 73rd European Atherosclerosis Society Congress #150, Salzburg, Austria 2002) report H.E.L.P. (heparin-mediated extracorporeal LDL/fibrinogen precipitation) apheresis for the treatment of acute myocardial infarction suffering from diffuse transplant coronary artery disease, incorporated herein by reference in its entirety.

Otto and associates (Proceedings of 73rd European Atherosclerosis Society Congress #185, Salzburg, Austria 2002) report long-term reduction of C-reactive protein by LDL apheresis leading to reduced risk for cardiovascular events, incorporated herein by reference in its entirety.

Konovalov and associates (Proceedings of 73rd European Atherosclerosis Society Congress #259, Salzburg, Austria 2002) report LDL apheresis leading to stabilization and even regression of atherosclerotic plaques in coronary arteries, incorporated herein by reference in its entirety.

Moriarty and associates (Proceedings of 73rd European Atherosclerosis Society Congress #511, Salzburg, Austria 2002) report H.E.L.P. (heparin-mediated extracorporeal LDL/fibrinogen precipitation) apheresis for lowering cholesterol with reduction of inflammatory markers and rheological improvement as an early intervention in acute coronary syndromes, incorporated herein by reference in its entirety.

Kostner and associates (Proceedings of 73rd European Atherosclerosis Society Congress #754, Salzburg, Austria 2002) report an extracorporeal solvent extraction procedure that removes essentially all cholesterol and triglyceride from treated plasma while not affecting blood constituents, incorporated herein by reference in its entirety.

It is one aspect of the present invention to provide a method of plasma purification, including delipidation and removal of unwanted elements (for example, toxins, viral particle, metabolic substances, and plasma constituents implicated in disease, such as complement or antibodies), for a patient comprising treating the patient's plasma through a plasma filtration apparatus having an orbital motion and returning the purified plasma back to the patient.

Applications for Enhanced Apheresis

In one aspect of the present invention, the enhanced apheresis enables quality platelet collection, wherein platelet can be collected directly from whole blood using the blood filtration apparatus having an orbital motion of the present invention with a proper membrane. It is another embodiment of the present invention to facilitate platelet collection by filtering the cell-less plasma after cells have been removed from the whole blood supply in a prior separation process.

In another aspect of the present invention, the enhanced apheresis enables quality viral particle removal with a proper membrane effective to allow sufficient amount of virus-free filtrate to pass through, wherein the viral particle can be removed because of its size, shape, affinity to the membrane, or anti-virus coating on the membrane.

In some aspect of the present invention, the enhanced apheresis enables quality cell washing and processing for stem cell selection and/or the bone marrow purging, wherein stem cells can be collected from the bone marrow or other sources using the filtration apparatus characterized by an orbital motion for the filtering membrane of the present invention with a proper membrane and at least one filtration step effective to allow sufficient amount of stem cells to be collected. In one embodiment, each filtration step may comprise a proper membrane for each specific filtering need. It is one object of the present invention to provide a method of cell washing for a patient comprising introducing a fluid supply into a filtration apparatus with a proper filtering membrane characterized by an orbital motion, wherein the fluid supply comprises cellular components and filtrate; treating the fluid supply through the filtration apparatus; separating cellular components from filtrate; and collecting purified filtrate. It is another object of the present invention to provide a second fluid supply comprising the separated cellular components with proper filtrate are introduced into a second filtration apparatus with a second filtering membrane characterized by an orbital motion for enhanced cell washing.

In still another aspect of the present invention, the enhanced apheresis enables quality red blood cell collection using the filtration apparatus having an orbital motion of the present invention with a proper membrane configured and sized for separating red blood cells from the whole blood with one step or multiple step filtration. The enhanced apheresis of the present invention is also applicable to auto-transfusion during surgery by returning red blood cells, white blood cells and platelets to the patient. The multiple step filtration is generally carried out by re-circulating a partially purified filtrate to a filtration apparatus.

In one further aspect of the present invention, the membrane surface may be modified, for example, treated with heparin enabling passing platelet or fibrinogen without clogging the membrane pores. In one embodiment, the membrane surface may be coated with an antibody for selectively removing the counterpart antigen in the fluid supply. In another embodiment, the membrane surface may be coated with an antigen for selectively removing the counterpart antibody in the fluid supply, for example used in autoimmune therapy. Multiple sclerosis (MS) is one example of the autoimmune diseases. In still another embodiment, the membrane surface may be treated by changing the charge characteristics on the membrane or add functional groups such as a hydroxyl group suitable for enhancing selective filtering a specific molecule or particulate constituent from the fluid supply.

From the foregoing description, it should now be appreciated that an enhanced plasmapheresis apparatus and methods for using same comprising a filter membrane under an orbital motion that has optimal local shear forces and maximum plasma flow output have been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method of treating autoimmune conditions of a patient comprising filtering the patient's blood through a blood filtration apparatus in an orbital motion having a filter membrane means for separating a plasma constituent from the blood and returning cellular components of the patient's blood back to said patient, wherein the filtering step is carried out with the blood filtration apparatus comprising a chamber having a hollow interior enclosed by a first plate, a second plate, and a flexible seal element between the first plate and the second plate, wherein the first plate is either essentially parallel to or at an acute angle to the second plate so as to form a chamber gap for the hollow interior; means for directing blood into the chamber gap; a non-rotational drive structure; said second plate comprising the filter membrane means for separating plasma constituent from the blood, wherein the second plate is detachably coupled to said non-rotational drive structure that controls the second plate in an orbital motion in reference to a center axis of the first plate; a collecting means; means for directing the plasma constituent passing through said filter membrane means to said collecting means; and means for directing from the chamber gap a remaining constituent of the blood out of the chamber.

2. The method of claim 1, wherein the autoimmune disease comprises multiple sclerosis.

3. The method of claim 1, wherein the filtering step is carried out with removing autoantibody from the patient's blood.

4. A method of plasma purification, wherein said plasma comprises at least one unwanted element, the method comprising treating said plasma through a plasma filtration apparatus with a filtering membrane effective for separating the at least one unwanted element from the plasma, wherein the filtration apparatus is operated in an orbital motion.

5. The method of claim 4, wherein the treating step is carried out with the plasma filtration apparatus comprising a chamber having a hollow interior enclosed by a first plate, a second plate, and a flexible seal element between the first plate and the second plate, wherein the first plate is either essentially parallel to or at an acute angle to the second plate so as to form a chamber gap for the hollow interior; means for directing the plasma into the chamber gap; a non-rotational drive structure; said second plate comprising the filter membrane for separating the at least one unwanted element from the plasma, wherein the second plate is detachably coupled to said non-rotational drive structure that controls the second plate in an orbital motion in reference to a center axis of the first plate; a collecting means; means for directing the separated plasma passing through said filter membrane means to said collecting means; and means for directing from the chamber gap a remaining constituent of the plasma wit the unwanted element out of the chamber.

6. The method of claim 4, wherein the at least one unwanted element comprises low density lipoprotein (LDL).

7. The method of claim 6, wherein the treating step for separating LDL from the plasma comprises immunadsorption apheresis, wherein an LDL-specific immune factor is loaded onto the filtering membrane of the filtration apparatus effective for immunadsorption apheresis.

8. The method of claim 6, wherein the treating step for separating LDL from the plasma comprises dextran sulfate adsorption apheresis, wherein an LDL-specific dextran sulfate is loaded onto the filtering membrane of the filtration apparatus effective for dextran sulfate adsorption apheresis.

9. The method of claim 6, wherein the treating step for separating LDL from the plasma comprises heparin-induced extracorporeal LDL precipitation apheresis, wherein an LDL-specific heparin is loaded onto the filtering membrane of the filtration apparatus effective for heparin-induced extracorporeal LDL precipitation apheresis.

10. The method of claim 9, wherein the heparin-induced extracorporeal LDL precipitation apheresis further comprises fibrinogen removal.

11. The method of claim 4, wherein the at least one unwanted element comprises viral particle.

12. The method of claim 4, wherein the at least one unwanted element comprises toxins.

13. The method of claim 4, wherein the at least one unwanted element comprises metabolic substances.

14. The method of claim 4, wherein the at least one unwanted element comprises complement.

15. The method of claim 4, wherein the at least one unwanted element comprises autoantibody.

16. A method of cell washing for a patient comprising: introducing a fluid supply into a filtration apparatus with a proper filtering membrane, wherein the filtration apparatus is operated in an orbital motion, wherein the fluid supply comprises cellular components and filtrate; treating the fluid supply through said filtration apparatus; separating cellular components from filtrate; and collecting purified filtrate.

17. The method of claim 16, wherein the separated cellular components are stem cells.

18. The method of claim 16, wherein the fluid supply comprises bone marrow from the patient.

19. The method of claim 16 further comprising introducing a second fluid supply comprised of the separated cellular components with proper filtrate into a second filtration apparatus with a second filtering membrane characterized by an orbital motion for enhanced cell washing.

* * * * *